United States Patent [19]

Riviere

[11] Patent Number: 5,620,416
[45] Date of Patent: Apr. 15, 1997

[54] METHODS OF USING TOPICAL AGENTS WITH SYSTEMICALLY ADMINISTERED ACTIVE AGENTS

[75] Inventor: Jim E. Riviere, Raleigh, N.C.

[73] Assignee: North Carolina State University, Raleigh, N.C.

[21] Appl. No.: 473,318

[22] Filed: Jun. 7, 1995

[51] Int. Cl.$^6$ .................................................... A61M 31/00
[52] U.S. Cl. ............................... 604/49; 604/20; 604/290
[58] Field of Search ........................... 604/20–21, 48–53, 604/890.1, 289–290, 304, 306; 602/48–51; 424/447–449; 514/929, 946–947

[56] References Cited

U.S. PATENT DOCUMENTS

| | | | |
|---|---|---|---|
| 4,650,484 | 3/1987 | Shaw et al. | 604/897 |
| 4,849,226 | 7/1989 | Gale . | |
| 5,302,172 | 4/1994 | Sage, Jr. et al. | 604/20 |
| 5,334,138 | 8/1994 | Sage, Jr. et al. | 604/20 |

OTHER PUBLICATIONS

C. Amsellem, et al., *Potentializing effect of ketoconazole on cyclosporin A–induced inhibition of keratinocyte DNA synthesis* Acta Derm. Venereol. (Stockh, 74:257–259 (1994).

J.E. Riviere et al. *Determination of lidocaine concentrations in skin after transdermal iontophoresis: Effects of vasoactive drugs* Pharmaceutical Research, 9:211–214 (1992).

J.E. Riviere et al., *Effects of Vasoactive drugs on transdermal lidocaine iontophoresis*; J. Pharmaceutical Sciences 80:615–620 (1991).

J.E. Riviere et al., *Nonuniform alteration of cis–diamminedichloroplatinum(II) tissue distribution in dogs with whole body hyperthermia*, Cancer Research 50:2075–2080 (1990).

*Primary Examiner*—Mark Bockelman
*Attorney, Agent, or Firm*—Bell, Seltzer, Park & Gibson

[57] ABSTRACT

The present invention relates to the simultaneous administration of topical agents and systemic active agents to treat diseases of the skin and surrounding tissues, wherein the topical drug is applied to a treatment area and affects the concentration or activity of the systemic drug in that area.

7 Claims, No Drawings

METHODS OF USING TOPICAL AGENTS WITH SYSTEMICALLY ADMINISTERED ACTIVE AGENTS

FIELD OF THE INVENTION

The present invention relates to the use of topically applied agents in conjunction with systemically administered active agents to treat diseases of the skin and surrounding tissues, wherein the topical agent is applied on or near an area in need of treatment by the systemically administered active agent. The topical agent acts to potentiate the effects of the systemically administered agent in the treatment area, or to target the systemically administered agent to that area. Alternatively, the topical agent may act to lessen the effects of the systemically administered agent in the treatment area.

BACKGROUND OF THE INVENTION

Various methods have been utilized to target a pharmaceutical agent to a specific tissue or anatomic area in need of treatment. Most commonly the active agent is administered directly to the treatment site, for example, by injection. Such targeted delivery is desirable where the area in need of treatment is localized or where systemic delivery may result in toxicity. In treating diseases and lesions of the skin and surrounding tissues, active agents are often administered topically.

Diverse substances have been used in conjunction with topically applied active agents to increase the delivery of the active agent across the barrier of the skin. The delivery of active chemotherapeutic agents across the skin has been modified by simultaneous topical use of penetration enhancing agents such as Azone (1-dodecylazacycloheptane-2-one) or 1-[2-(decylthio)ethyl]azacyclopentane-2-one (HPE-101). Uekama et al., *J. Pharm. Pharmacol.* 44:119–121 (1992). Parab U.S. Pat. No. 5,087,620 describes compositions for topical use containing asteroid as the active agent and imidazole or imidazole derivatives as penetration enhancers. Other penetration enhancers include surfactants such as sodium lauryl sulfate.

Sage et al. U.S. Pat. No. 5,334,138 describes the co-iontophoresis of a vasoconstrictor and an active agent, where the vasoconstrictor acts to enhance the iontophoretic delivery of the active agent. Sage et al. U.S. Pat. No. 5,302,172 describes the co-iontophoresis of an active agent and a vasodilator, where the vasodilator acts to increase the amount of active agent delivered iontophoretically.

Other methods have been designed to target a systemically delivered agent to a particular treatment site. Radiolabelled monoclonal antibodies have been used to target radiation therapy to various tumor types, while whole body hyperthermia has been proposed as a means of targeting systemic platinum therapy to specific tissue types (Riviere et al., *Cancer Research* 50:2075–2080 (1990).

SUMMARY OF THE INVENTION

A first aspect of the present invention is a method of providing an increased concentration of a systemically administered active agent to a treatment area of a subject, comprising systemically administering an active agent to the subject and topically applying a vasodilator to the treatment area in an amount effective to increase the concentration of active agent in the treatment area.

A further aspect of the present invention is a method of providing a decreased concentration of a systemically administered active agent to a treatment area of a subject area, comprising systemically administering an active agent to a subject and topically applying a vasoconstrictor to the treatment area of the subject in an amount effective to decrease the concentration of the active agent in the treatment area.

The foregoing and other objects and aspects of the present invention are explained in detail in the specification set forth below.

DETAILED DESCRIPTION OF THE INVENTION

The present methods utilize a topically applied agent to target a systemically administered active agent to a selected treatment site. The topical agent may act to preferentially concentrate the active agent in the treatment site, or to prolong the pharmaceutical action of the active agent in the treatment site.

Additionally, the present methods utilize a topically applied agent to protect a treatment site from a systemically administered active agent. The topical agent may prevent the active agent from reaching or residing in the treatment site, or may inactivate any systemic agent within the treatment site.

Various combinations of topical and systemic agents may be used in the present methods to target a systemically administered active agent to a treatment site, or conversely to protect a treatment site from a systemically administered active agent.

Topically delivered vasoactive agents act on the dermal vasculature. The topical administration of a vasodilator to a treatment area can act to increase delivery of a systemic active agent to that area by increasing the area of the capillary membrane across which delivery of the active agent occurs, and/or increasing the volume of blood present (and hence the amount of active agent) in the treatment area as a whole. The topical administration of a vasoconstrictor to a treatment area can act to decrease delivery of a systemic active agent to that area by decreasing the area across which delivery of the active agent occurs, and/or decreasing the volume of blood (and hence the amount of active agent) in the treatment area as a whole. The increase or decrease of the systemic agent in the treatment area is relative to that in similar anatomic sites which have not been treated with the topical vasoactive agent. As used herein, treatment area or treatment site refers to the skin on which the topical agent is applied, as well as the underlying tissues which are affected by the topical agent. Underlying tissues which can be affected by the topical agent include but are not limited to fat, muscle, tendons, bursae, and joints. The area affected by the topical agent will depend on the topical agent selected and the method of topical administration.

Many systemically administered chemotherapeutic drugs are taken into cells and remain active until intracellular metabolizing enzymes break down the active agent. Topical administration of enzyme inhibitors will prevent the enzymatic breakdown of chemotherapeutic agents, and increase the concentration of the chemotherapeutic drug in that area and/or extend the activity of the chemotherapeutic drug in the treatment area. Alternatively, where it is desirable to reduce the activity of a systemically administered chemotherapeutic agent in a selected treatment area, metabolic agents which act to break down systemically administered chemotherapeutic agents may be applied topically to that area. The increase or decrease of the systemic agent's concentration or activity in the treatment area is measured relative that in similar anatomic sites which have not been treated with the topical agent.

It is known that many cancer and some normal cells minimize their susceptibility to chemotherapeutic agents by expelling intracellular drug molecules using specific transport proteins. P-glycoprotein has been identified as one such transport protein responsible for resistance of cancer cells to chemotherapeutic agents (Gottesman and Pistin, *Ann. Rev. Biochem*, 62:385–427 (1993)). It is further known that many compounds, such as cyclosporin and its analogs, inhibit the activity of p-glycoprotein (see, e.g., Gottesman and Pistin (1993)). Topical application of an inhibitor of intracellular transport proteins in areas in need of treatment with antineoplastic chemotherapeutic agents will potentiate the activity of systemically administered chemotherapeutic agents by slowing the rate of expulsion of the agent from cells. Topical cyclosporin acts to reduce the expulsion of chemotherapeutic agents by p-glycoprotein from cells in an area so treated, and will thus increase the concentration and/or extend the activity of the chemotherapeutic agent in the treatment area. The increase in concentration or activity in the treatment area is measured relative that in similar anatomic sites which have not been treated with the topical inhibiting agent.

Peptide and protein therapeutic agents include monoclonal and polyclonal antibodies, antigens, enzymes, hormones, immune factors and blood clotting factors. Oral administration of peptide and protein therapeutic agents is limited by the degradation of these agents which occurs in the gastrointestinal tract, as well as by the extensive hepatic first-pass elimination of peptides and proteins which are absorbed into the blood stream. As a result, most therapeutic peptide/protein agents are given parenterally. Yet the efficacy of parenterally delivered protein or peptide agents is hampered due to the difficulty of such large agents in crossing the capillary membrane. Topical administration of an agent which increases capillary permeability will enhance delivery of parenterally administered agents which otherwise would be unable or poorly able to cross the capillary membrane due to size. Histamine and agents with histamine-like activity (such as vasoactive peptides and some cytokines such as interleukin II) are postulated to enhance capillary permeability. The increase in concentration or activity in the treatment area is measured relative that in similar anatomic sites which have not been treated with the topical agent to increase capillary permeability.

Specific binding of therapeutic antibodies to the corresponding antigens acts to target the antibodies to specific locations. However, non-specific binding of therapeutic antibodies is commonly encountered and may cause toxicity or otherwise limit the use of the therapeutic antibody. Topical agents which promote expression of antigens which bind to a selected therapeutic antibody can be utilized to increase the delivery of therapeutic antibodies to a treatment site. Alternatively the antigen itself may be delivered to the treatment site. The increase in delivery and/or concentration in the treatment area is measured relative that in similar anatomic sites which have not been treated with the antigen-promoting agent. Examples of systems which may be utilized to increase the binding of an antibody to a treatment site include the avidin-biotin binding system and antigen binding fragments.

1. Systemic Administration

As used herein, systemic administration of an agent refers to modes of administration whereby the active agent is delivered essentially throughout the subject's body. Systemically administered agents are most typically placed into the blood stream, where they are then distributed throughout the body by the normal flow of blood. Exemplary modes of systemic administration are oral and parenteral administration. The major routes of parenteral administration are intravenous, subcutaneous, and intramuscular. Absorption from subcutaneous and intramuscular sites of administration occurs by simple diffusion along the gradient from drug depot to blood plasma. The area of the absorbing capillary membranes and the solubility of the active agent in the interstitial fluid limits the rate of absorption. Oral administration of an agent with subsequent uptake of the agent from the gastrointestinal tract to the blood also results in systemic delivery.

2. Topical administration

As used herein, topical administration refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration of a pharmaceutical agent can result in a limited distribution of the agent to the skin and surrounding tissues or, when the agent is removed from the treatment area by the bloodstream, can result in systemic distribution of the agent. For example, application of antidiuretic hormone to the nasal mucosa results in systemic absorption. Topical administration of pharmaceutical agents is widely used in treating dermatologic conditions. In some situations, agents applied topically may be absorbed into the bloodstream so rapidly as to have systemic toxicity.

3. Skin

The skin (cutis) comprises the epidermis and the dermis, as well as the blood vessels located within the dermis. The epidermis is the outer epithelial portion of the skin and includes the stratum corneum. The dermis underlies the epidermis and includes a layer of dense, irregular connective tissue, as well as blood and lymphatic vessels, nerves and nerve endings, glands and hair follicles. Underlying the dermis is the hypodermis (tela subcutanea) which includes fat, the superficial fasciculi of muscular tissue, and the cutaneous vessels and nerves. Mucous membranes do not include the stratum corneum and the connective tissue underlying the mucous membranes is generally not termed dermis.

4. Transdermal delivery

Passive transdermal delivery relies on the diffusion of an agent across the barrier of the skin; the rate limiting barrier is the stratum corneum. The epidermis acts as a lipid barrier and few pharmaceutical agents are able to penetrate intact skin. In contrast, the dermis is permeable to many solutes and absorption of drugs therefor occurs more readily through skin which is abraded or otherwise stripped of the epidermis to expose the dermis. Absorption through intact skin can be enhanced by placing the active agent in an oily vehicle before application to the skin (a process known as inunction). Passive topical administration may consist of applying the active agent directly to the treatment site in combination with emollients or penetration enhancers.

In active transdermal delivery the active agent is driven across the skin at a rate higher than that which can be achieved using passive transdermal delivery methods. An exemplary method of active transdermal delivery is iontophoresis, which utilizes an electric current to drive ions or ionic compounds across the skin.

Both passive and active transdermal delivery are suitable for use in the present methods, including inunctation, use of gels or ointments with patches or other occlusive dressings, iontophoresis and other electrically assisted transdermal delivery modes, phonophoresis, electroosmosis, and electroporation.

As used herein, an effective or delivery-enhancing amount of a topically administered agent means that amount needed to produce the desired concentrating or enhancing effect with regards to the systemically delivered active agent. The delivery-enhancing amount will vary depending on the particular combination of systemically delivered active agent and topically applied agent, the physiological effects of both the active agent and topical agent, as well as the condition being treated and the age, species and condition of the subject treated.

5. Iontophoretic Delivery

Iontophoresis is the movement of ionized or charged species by application of an electrical current. During transdermal iontophoretic administration of an active agent, charged compounds placed in an electrolytic medium migrate from a reservoir attached to the skin of a subject into the dermal tissue beneath the reservoir. The movement of the ions or ionic substances in the electrolytic medium is induced with the flow of electric current, typically produced by two electrodes placed against the subject's skin. The rate of agent delivery is a function of current, charged compound, and the presence of other ions in the reservoir. Iontophoretic delivery of charged therapeutic agents has been used with, for example, anesthetics and anti-inflammatory drugs to achieve localized effects in the skin.

The use of iontophoresis in the present methods is not limited to any one iontophoretic system. Iontophoretic devices typically include at least two electrodes which are attached to the skin surface, an electrical energy source, and a reservoir containing the active agent to be delivered.

Modification of active agents for delivery using iontophoresis follows well-known principles. In delivering a positively charged drug, the chloride or hydrochloride form of the drug can be made and placed in the reservoir of the iontophoretic device for delivery. See, e.g., *Remington's Pharmaceutical Sciences,* Ed. Arthur Osol, 16th Ed., 1980, Mach Publishing Co., Easton, Pa. Depending on whether the anionic or cationic form of the active agent is to be delivered, the basic (OH— or amine) or acid (H+) form of the active agent is made. The composition to be delivered is typically dissolved in a suitable solvent to provide the ionic form of the active agent for delivery. Suitable solvents include but are not limited to water, glycerine, lower alkyl alcohols such as methyl alcohol, ethyl alcohol, and branched alcohols such as isopropyl alcohol.

In the methods of the present invention, the amount of a topical agent to be iontophoresed is a function of the particular topical agent being used and the particular systemically administered active agent. The amount of active agent provided to the selected treatment site and the overall systemic concentration of active agent may be ascertained using methods well known in the art. By knowing the iontophoretic conditions and measuring the amount of active agent delivered to the treatment site and the overall systemic concentration of active agent, a useful range of delivery conditions for a systemic active agent/topical agent combination may be ascertained.

6. Active Agent

As used herein, active agent refers to a biologically active compound that has a therapeutic, prophylactic pharmacological, or physiological, effect on the subject to which it is administered. Active agents used in the methods of the present invention may be provided as prodrugs or in combination with other substances. Active agents suitable for use in the methods of the present invention include but are not limited to antiarthritics, antiasthma agents, anticholinergics, antivirals, antineoplastics, anti-inflammatories, analgesics, antibacterials, antibiotics, antithrombotics, antifungals, antipruritics, muscle relaxants, antihistamines, antibiotics, corticosteroids, anesthetics, anti-psoriasis agents, antihelmintics, vasodilators, vasoconstrictors, diagnostics, hormones and immunomodulators.

The systemically administered active agent may be delivered in any suitable pharmaceutically acceptable composition, and may include additional substances such as stabilizers and carriers, as is known in the pharmaceutical art.

As used herein, an effective amount of active agent refers to that amount needed to produce the intended therapeutic effect at the treatment site when used in the methods of the present invention (i.e., an effective therapeutic amount). The effective amount will depend upon the systemically delivered active agent and the topically administered agent used, as well as the condition being treated and the age, condition, and species of the subject being treated. A range of useful dosages of a topically administered agent in combination with a given systemically administered agent is determined by analyzing the effects of the active agent at the treatment site while considering any potential systemic side effects. Methods to determine the proper dosages of specific compounds would be apparent to one skilled in the pharmaceutical arts. The combined use of topical and systemic agents in the present methods may decrease the total dosage of systemic agent required to achieve a therapeutic effect in a defined treatment area.

The term pharmaceutically acceptable composition refers to compositions containing salts, carriers, diluents and other pharmaceutically acceptable additives as are known in the art which do not adversely affect the properties of the active agent. Pharmaceutically acceptable compositions can be prepared with reference to general texts in the field.

The term active agent is used herein to refer to the systemically administered active agent; the term topical agent is used herein to refer to the topically administered agent. The topically administered agents are also biologically active compounds that have a therapeutic, prophylactic pharmacological, or physiological effect on the subject to which they are administered.

7. Topical Agents

Topical vasoactive agents suitable for use in the present methods include both vasoconstrictors and vasodilators, depending on the desired effect and the active agent being delivered systemically. Suitable vasoconstrictors include but are not limited to α-adrenergic agonists, imidazoline vasoconstrictors, adrafinil, adrenolone, amidephrine, apraclonidine, budralazine, clonidine, cyclopentamine, detomidine, dimetofrine, dipivefrin, epherine, fenoxazoline, guanabenz, guanfacine, hydroxyamphetamine, ibopamine, indanazoline, isometheptene, mephentermine, metaraminol, methoxamine hydrochloride, methylhexaneamine, metizoline, midodrine, naphazoline, norepinephrine, norfenefrine, octodine, octopamine, oxymetazoline, phenylephrine hydrochloride, phenylpropanolamine hydrochloride, phenypropylmethylamine, pholedrine, propylhexedrine, pseudoephedrine, rilmenidine, synephrine, tetrahydrozaline, tiamenidine, tramazoline, tuaminoheptane, tymazoline, tyramine, and xylometazoline.

Suitable vasodilators include but are not limited to peripheral vasodilators such as aluminum nicotinate, bamethan, bencyclane, betahistine, bradykinin, bovincamine, bufeniode, buflomedil, butalamine, cetiedil, ciclonicate, cinepaside, cinnarizine, cyclandelate, diisopropylamine dichloroacetate, eledoisin, isosorbide dinitrate (ISDN), isoxsuprine, kallidin, kallikrein, moxisylyte, nafronyl, nicametate, nicergoine, nicofuranose, nicotinyl alcohol, nylidrin, pentifylline, pentoxifylline, piribedil, prostaglandin $E_1$, suloctidil, tolazoline, and xanthinol niacinate.

Additional suitable vasodilators may be selected from the coronary vasodilators, such as amotriphene, bendazol, befurodil hemisuccinate, benziodarone, chloracizine, chromonar, clobenfurol, clonitrate, dilazep, dipyridamole, droprenilamine, efloxate, erythritol, erythrityl tetranitrate, etafenone, fendiline, floredil, ganglefene, hexestrol bis (B-diethylaminoethyl ether), hexobendine, itramin tosylate, khellin, lidoflazine, mannitol hexanitrate, medibasine, nicorandil, nitroglycerin, pentaerythritol tetranitrate, pentrinitrol, perhexiline, pimefylline, prenylamine, propatyl nitrate, pyridofyline, trapidil, tricromyl, trimetazidine, trolnitrate phosphate, and visnadine.

Additional suitable vasodilators may be selected from the cerebral vasodilators, such as bencyclane, cinnarizine, citicoline, cyclandelate, ciclonate, diisopropylamine dichloroacetate, eburnamonine, fenoxidil, flunarizine, ibudilast, ifenprodil, nafronyl, nicametate, nicergoline, nimodipine, papaverine and penifylline.

Vasodilators selected from the class of peripheral vasodilators are preferred in the present methods.

8. Subjects

The present methods may be applied to human as well as non-human subjects, and thus has both medical and veterinary applications. Suitable subjects include, but are not limited to, humans and other primates, companion animals such as cats and dogs, livestock such as cattle, pigs and horses, laboratory animals such as rats and mice, and exotic species such as zoo animals.

The present methods are useful in treating diseases of the skin and underlying tissue, with the choice of active agent and treatment site dependent on the condition being treated, as would be apparent to one skilled in the art. Conditions which may be treated by the present methods include cancer and other neoplastic conditions; localized bacterial, fungal and viral infections of the skin and underlying tissues, including herpetic infections; musculoskeletal disorders such as arthritis; traumatic conditions such as blunt muscle trauma; and chronic skin conditions such as eczema and psoriasis. A more complete listing and description of conditions of the skin which may be treated using the present methods may be found in any standard dermatologic textbook, such as Textbook of Dermatology, 5th ed. Champion RH et al. Vols. 1–4, Blackwell Scientific Publications Cambridge Mass., (1992).

The following examples are provided to illustrate the present invention, and should not be construed as limiting thereof. In these examples, CDDP means cisdiaminedichloroplatinum, ISDN means isosorbide dinitrate, mAmp means milliampere, cm means centimeter, mg means milligram, kg means kilogram, ml means milliliter, and min means minutes.

EXAMPLE 1

Iontophoresis of a Vasoactive Agent with Systemic Administration of an Active Agent The ability of iontophoretically-delivered, vasoactive compounds to affect local cutaneous concentrations of a systemically delivered active agent was investigated in female weanling Yorkshire pigs. The effect of the timing of iontophoresis on tissue deposition of active agent was also investigated.

Study animals were assigned to receive iontophoresis either prior to, or after, attaining steady-state systemic concentrations of cisplatin (cisdiaminedichloroplatinum, CDDP). The iontophoresed agent was either a peripheral vasodilator (tolazoline), peripheral vasoconstrictor (norepinephrine), or saline.

Subjects were sedated with intramuscular ketamine/xylazine, and anesthesia was maintained with intravenous thiamylal. In each subject the inguinal area was divided into four quadrants, three of which received iontophoresis. One quadrant received iontophoresis of 0.4% tolazoline HCl (TOL); one received iontophoresis of 0.4% norepinephrine HCl (NOR); and one received iontophoresis of 50% saturated saline (SAL). The remaining quadrant served as a control (CON) and was not subjected to iontophoresis.

Iontophoretic current density was 0.2 mAmp/cm$^2$. Cisplatin (1.0 mg/ml) was infused via the saphenous vein at a rate of 0.03 mg/kg/min. Blood samples (3 ml) were drawn from the jugular vein every 15 minutes, placed in heparinized tubes and stored for subsequent platinum analysis to assure that steady-state CDDP concentrations had been reached. In subjects receiving iontophoresis prior to attaining steady-state CDDP levels, iontophoresis was carried out for 30 minutes, at which time CDDP infusion was started and maintained for 120 minutes. In subjects receiving iontophoresis after attaining steady-state CDDP levels, iontophoresis was started two hours after CDDP infusion began; phoresis and infusion continued simultaneously for 30 minutes. At termination of the treatment, skin samples were collected from each electrode site in each of the three iontophoresed quadrants, as well as from four sites in the control quadrant.

In subjects receiving iontophoresis prior to reaching steady-state CDDP concentrations, skin CDDP concentrations under tolazoline electrodes (4.93±0.66) were significantly greater (p=0.01) than those of control skin (2.26±0.17), whereas CDDP concentrations under norepinephrine electrodes (0.78±0.19) were significantly lower than those of control skin (p<0.001). When analyzed collectively, CDDP concentrations under all saline cathodes were greater than those of control skin (2.92±0.28 vs. 2.26±0.17, p<0.05).

In subjects receiving iontophoresis after reaching steady-state CDDP concentrations, skin CDDP concentrations did not vary significantly among skin samples from the control electrodes (2.02±0.1), tolazoline electrodes (2.48±0.49), norepinephrine electrodes (2.90±1.09) and saline electrodes (2.75±0.65).

TABLE 1

| Treatment | Ionto. prior to CDDP | Ionto. after CDDP |
|---|---|---|
| 0.4% Tolazoline | 4.93 ± 0.66 | 2.48 ± 0.49 |
| 0.4% Norepineph. | 0.78 ± 0.19 | 2.90 ± 1.09 |
| 50% saline | 2.92 ± 0.28 | 2.75 ± 0.65 |
| Control | 2.26 ± 0.17 | 2.02 ± 0.10 |

EXAMPLE 2

Application of Vasodilator Agents

Four weanling female Yorkshire pigs were utilized to study the effects of passive topical application of the vasodilator agents ISDN and nitroglycerin on local cutaneous concentrations of intravenously infused cisplatin (CDDP).

The inguinal region of each subject was divided into upper left, upper right, lower left, and lower right quadrants. One quadrant per subject received topical ISDN, applied using a topical patch containing 22 mg ISDN in a 20 cm$^2$ patch (also containing standard delivery agents). One quadrant per subject received topical nitroglycerin, (commercial Nitrodur® patch, 40 mg in 10 cm$^2$ patch, Key Pharmaceuticals). The remaining two quadrants served as controls. Treatments were rotated among the quadrants between the subjects. The vasodilator agents were applied to their respective quadrants at the same time; thirty minutes later intravenous CDDP infusion was started as described in Example 1, above. CDDP infusions continued for 120 minutes, at which time the animals were euthanized and four skin samples per quadrant were collected.

Mean CDDP concentrations in skin treated with ISDN or NTG were compared with control skin (TABLE 2). These results are provided without regard to quadrant. Pretreatment with either ISDN or NTG significantly increased skin CDDP concentrations as compared to controls ($p<0.001$ and $p<0.005$, respectively), with ISDN pretreatment resulting in the greatest skin CDDP concentrations. ISDN- and NTG-pretreated skin samples were also significantly different from each other.

As seen in TABLE 3, regional variations in CDDP concentration were seen. Among quadrants serving as controls, CDDP concentrations tended to be greater in the upper quadrants, with the upper right control quadrant having significantly greater concentrations of CDDP than either of the lower control quadrants. When pretreated with ISDN, the same trend of increased CDDP concentration in the upper quadrants is seen. While similar to each other, both upper quadrants contained significantly greater CDDP concentrations than did the lower left quadrant. Regional variations were not seen when skin was pretreated with NTG, however, and upper right quadrant CDDP concentrations were similar to those of the lower quadrants.

These results indicate that pretreatment with topical ISDN and NTG significantly increased local skin concentrations of intravenously administered CDDP. Regional variations in concentration appear to exist. Such regional variation appears to be completely masked by pretreatment with NTG.

TABLE 2

| Treatment | Skin Conc. CDDP | % of Control |
|---|---|---|
| Control | 1.60 ± 0.05 | 100 |
| NTG | 1.91 ± 0.05** | 119 |
| ISDN | 2.18 ± 0.07*** | 136 |

**$p < 0.005$
***$p < 0.001$

TABLE 3

| Treatment | UR Quadrant | UL Quadrant | LR Quadrant | LL Quadrant |
|---|---|---|---|---|
| Control | 1.79a | 1.73ab | 1.47b | 1.45b |
| ISDN | 2.36a | 2.19a | — | 1.81b |
| NTG | 1.99a | — | 1.95a | 1.85a | a,b = values within a treatment group that have different letters are significantly different from one another ($p < 0.05$).
— = study not done.

The foregoing is illustrative of the present invention and is not to be construed as limiting thereof. The invention is defined by the following claims, with equivalents of the claims to be included therein.

That which is claimed is:

1. A method of providing an increased concentration of a systemically administered active agent to a treatment area of a subject, comprising:

systemically administering an active agent to a subject, subject to the provisos that said active agent is other than a vasodilator and that systemic administration is by means other than iontophoresis; and topically applying a vasodilator to a treatment area of the subject in an amount effective to increase the concentration of said active agent in the treatment area, wherein the concentration of systemically administered active agent is increased in the treatment area compared to the concentration of systemically administered active agent which would be achieved in the treatment area in the absence of topical vasodilator.

2. A method according to claim 1, wherein said systemically administered active agent is selected from the group consisting of antiarthritics, antivirals, antineoplastics, anti-inflammatories, antibacterials, antifungals, antipruritics, muscle relaxants, antihistamines, antibiotics, corticosteroids, anesthetics, anti-psoriasis agents, and antihelmintics.

3. A method according to claim 1 wherein said vasodilator is selected from the group consisting of cerebral vasodilators, coronary vasodilators, and peripheral vasodilators.

4. A method according to claim 1 wherein said vasodilator is selected from the group consisting of nitroglycerin, ISDN and tolazoline.

5. A method according to claim 1, wherein said vasodilator is applied topically prior to systemic administration of said active agent.

6. A method according to claim 1, wherein said vasodilator is applied topically at the same time as systemic administration of said active agent.

7. A method according to claim 1, wherein said vasodilator is applied iontophoretically.

* * * * *